United States Patent [19]

Karami

[11] 4,212,302
[45] Jul. 15, 1980

[54] ABSORBENT ARTICLE WITH SPACED HYDROCOLLOID MATERIAL

[75] Inventor: Hamzeh Karami, Crystal Lake, Ill.

[73] Assignee: Colgate-Palmolive Company, New York, N.Y.

[21] Appl. No.: 863,484

[22] Filed: Dec. 22, 1977

Related U.S. Application Data

[63] Continuation of Ser. No. 712,439, Aug. 9, 1976, abandoned.

[51] Int. Cl.³ .............................................. A61F 13/16
[52] U.S. Cl. ................................................... 128/287
[58] Field of Search ............... 128/156, 284, 286, 287, 128/288, 290 R, 296

[56] References Cited

U.S. PATENT DOCUMENTS

| | | | |
|---|---|---|---|
| 3,344,789 | 10/1967 | Arnold et al. | 128/287 |
| 3,670,731 | 6/1972 | Harmon | 128/284 |
| 3,971,379 | 7/1976 | Chatterjee | 128/290 R |
| 4,005,712 | 2/1977 | Karami | 128/287 |
| 4,055,180 | 10/1977 | Karami | 128/284 |

FOREIGN PATENT DOCUMENTS 940284  1/1974  Canada ..................................... 128/287

*Primary Examiner*—C. Fred Rosenbaum
*Attorney, Agent, or Firm*—Powell L. Sprunger

[57] ABSTRACT

An absorbent article comprising, a fluid pervious top sheet, a backing sheet of fluid impervious material, and an absorbent pad intermediate the top and backing sheets. The pad has a fluid receiving region adjacent a central portion of the pad and a hydrocolloid material at a location spaced from the fluid receiving region, with the fluid receiving region being substantially free of the hydrocolloid material.

3 Claims, 6 Drawing Figures

4,212,302

ABSORBENT ARTICLE WITH SPACED HYDROCOLLOID MATERIAL

This is a continuation, of application Ser. No. 712,439 filed Aug. 9, 1976 and now abandoned.

BACKGROUND OF THE INVENTION

The present invention relates to absorbent articles.

A various assortment of absorbent articles, such as disposable diapers and sanitary napkins, have been proposed for absorbing and retaining body fluids. Such articles have been constructed with an absorbent pad having a relatively large volume of pad material, in order to provide the necessary absorbency and fluid holding capacity for the articles, which adds an undesired bulk to the articles. For example, disposable diapers are commonly made from a fluid impervious backing sheet, a fluid pervious cover sheet, and an absorbent pad, such as comminuted wood pulp known in the art as wood fluff, located between the backing and cover sheets. The pads of such conventional diapers are relatively bulky, resulting in a poor fit and minimal comfort to the infant.

More recently, it has been proposed to include highly absorbent materials, such as hydrocolloid polymers, in the pads. In theory, the hydrocolloid materials permit a reduction in pad bulk while increasing desirable absorbent and fluid holding characteristics of the pads, since such materials are capable of absorbing and retaining many times their weight in liquid, such as urine or other body fluids. In practice, use of such materials in absorbent articles has been limited due to difficulties caused by the nature of the materials.

It has been contemplated that the hydrocolloid materials may be placed in a central region of the articles at a location where body fluids, such as urine, are applied to the articles. However, the hydrocolloid materials swell and become gelatinous when wetted, and it has been found that the wetted materials form a film on the pad which decreases the rate of further fluid penetration into the pad. Thus, although the materials initially absorb the body fluids, they may later cause saturation and back wetting of the fluids in the central fluid receiving region of the articles. Moreover, in general it is desirable to retain the body fluids at a location spaced from the point of application to the articles in order to make maximum use of the pad.

SUMMARY OF THE INVENTION

A principal feature of the present invention is the provision of an absorbent article of simplified construction which absorbs and retains body fluids in an improved manner.

The article of the present invention comprises, a fluid pervious top sheet, a backing sheet of fluid impervious material, and an absorbent pad intermediate the top and backing sheets. The pad has a hydrocolloid material positioned in opposed margins of the pad adjacent opposed edges of the pad, and a fluid receiving region intermediate the pad margins adjacent a central portion of the pad being substantially free of the hydrocolloid material.

A feature of the present invention is that the hydrocolloid material enhances the absorbent and fluid holding capacity of the pad.

Another feature of the present invention is that body fluids are retained at pad locations spaced from the fluid receiving region in order to minimize the possibility of pad saturation in the fluid receiving region and to maximize use of the pad material.

Still another feature of the present invention is that the substantially free fluid receiving region prevents formation of a film by the hydrocolloid material which would otherwise decrease the rate of fluid passage into the pad.

Yet another feature of the invention is that in an embodiment the backing sheet includes opposed front margins overlying a front surface and the margins of the pad in order to encapsulate the hydrocolloid material with fluid impervious material and minimize the possibility of leakage from the pad margins.

Further features will become more fully apparent in the following description of the embodiment of this invention and from the appended claims.

DESCRIPTION OF THE PREFERRED EMBODIMENTS

Figure 1:
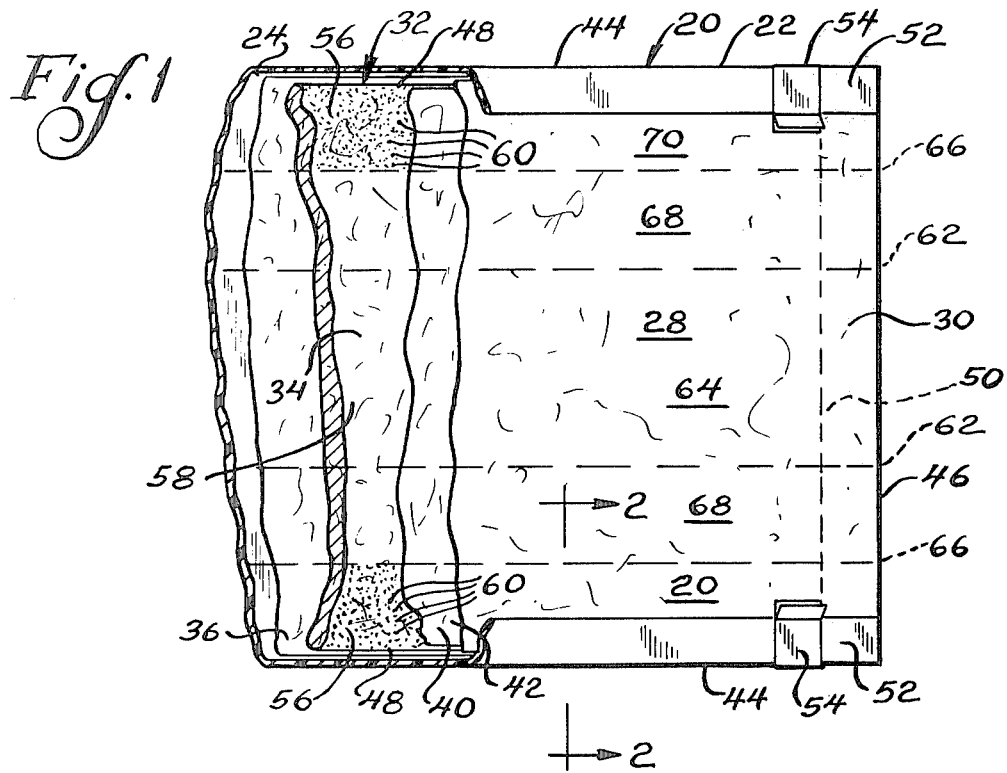
FIG. 1 is a fragmentary front plan view of an absorbent article of the present invention, shown in the form of a disposable diaper.
Figure 2:
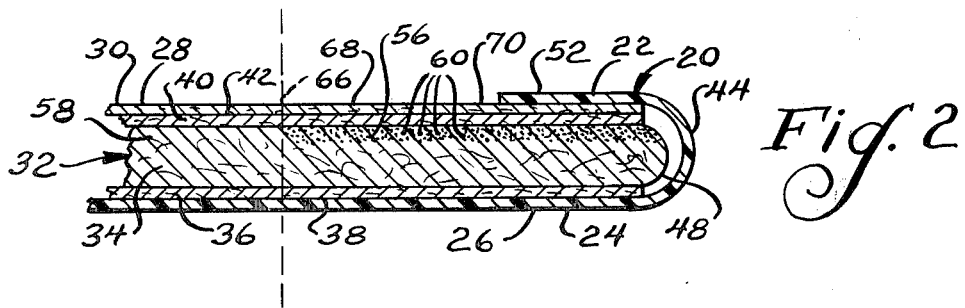
FIG. 2 is a fragmentary sectional view taken substantially as indicated along the line 2—2 of FIG. 1.

Referring now to FIGS. 1 and 2, there is shown an absorbent article generally designated 20 having an absorbent pad assembly 22. For convenience, the article 20 is disclosed in the form of a disposable diaper, although it will be understood that the invention is applicable to other absorbent articles, such as sanitary pads and maternity napkins.

The pad assembly 22 has a fluid impervious backing sheet 24, such as polyethylene, defining a back surface 26 of the article or diaper, a fluid pervious top or cover sheet 28 defining a front surface 30 for the diaper, and an absorbent pad 32 positioned intermediate the top sheet 28 and backing sheet 24. The absorbent pad 32 may have a pad portion 34 comprising a cellulosic material, such as one or more sheets of cellulosic wadding or comminuted wood pulp known in the art as wood fluff, a back wadding sheet 36 of cellulosic material defining a back surface 38 of the pad 32, and a front wadding sheet 40 of cellullosic material defining a front surface 42 of the pad 32. The front and back wadding sheets 40 and 36, respectively, provide structural integrity for the pad portion 34 during use of the article.

The pad assembly 22 has a pair of side edges 44 and end edges 46 connecting the side edges 44, and the absorbent pad 32 has a pair of side edges 48 and end edges 50 connecting the side edges 48. In a preferred form, the side edges 48 of the pad 32 are located adjacent the side edges 44 of the pad assembly 22, and the backing sheet 24 has lateral side margins 52 folded over and secured to the top sheet 28 over the pad 32. The diaper may also have tape fasteners 54 for use in securing the diaper about an infant during placement of the diaper.

Figure 3:
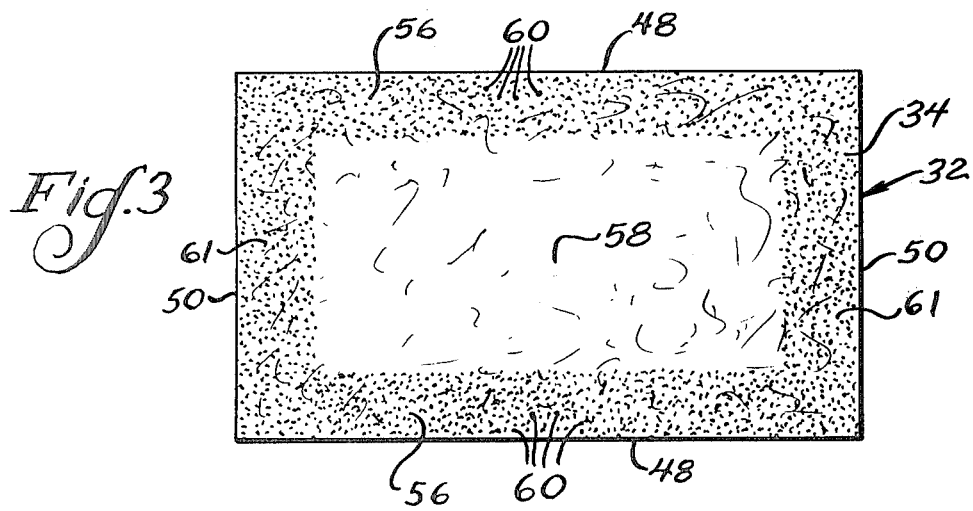
FIG. 3 is a plan view of an absorbent pad for the article of FIG. 1.

With reference to FIGS. 1-3, the pad 32 has a pair of lateral side margins 56 adjacent the pad side edges 48 and extending longitudinally between the end edges 50 of the pad, and a fluid receiving region 58 intermediate the side margins 56 in a lateral central portion of the pad 32. As shown, the lateral side margins 56 of the pad 32 have a hydrocolloid material 60, while the fluid receiving region at the point of application of body fluids to the pad 32 is substantially free of the hydrocolloid material. In a preferred form, the hydrocolloid material 60 is dispersed in the side margins 56 substantially between the end edges 50 of the pad 32. In an alternative form, with reference to FIG. 3, the hydrocolloid material may be located in end margins 61 of the pad adjacent the end edges 50 such that the fluid receiving region 58 is located in a longitudinal central portion of the pad intermediate the end margins 61, or the material 60 may be located in both the side and end margins 56 and 61 which surround the region 58.

The hydrocolloid material 60 may be of any suitable type, such as (a) hydrolyzed starch polyacrylonitrile copolymer H-span, Product 35-A-100, Grain Processing Corp., Muscatine, Iowa, disclosed in U.S. Pat. No. 3,661,815, (b) Product No. XD-8587.01L, which is cross-linked, Dow Corning Chemical Co., Midland, Michigan, (c) Product No. SGP 502S, General Mills Chemical, Inc., Minneapolis, Minnesota, (d) Product No. 78-3710, National Starch and Chemical Corp., New York, New York, (e) a hydrogel base product, Carbowax, a trademark of Union Carbide Corp., Charleston, West Virginia, or (f) base-saponisied starch-polyacrylonitrile and graft copolymers, United States Department of Agriculture, Peoria, Illinois, disclosed in U.S. Pat. No. 3,425,971. Such hydrocolloid materials have the capacity of absorbing many times their weight in liquids such as urine or other body fluids, and swell and form a gelatinous mass when wetted. In general, the hydrocolloid materials useful in the articles of the present invention may be organic or inorganic, are physiologically non-objectionable (non-toxic), and are characterized by swelling in the presence of water, by a relatively high affinity for water, and by normally at least partially assuming a suspension in the presence of water. Additionally, it has been found that the materials tend to form a film when wetted which impedes passage of body fluids into the pad if retained at the point of application of fluids into the pad, thus causing saturation of the pad and possible back wetting through the top sheet in the fluid receiving region.

Figure 6:
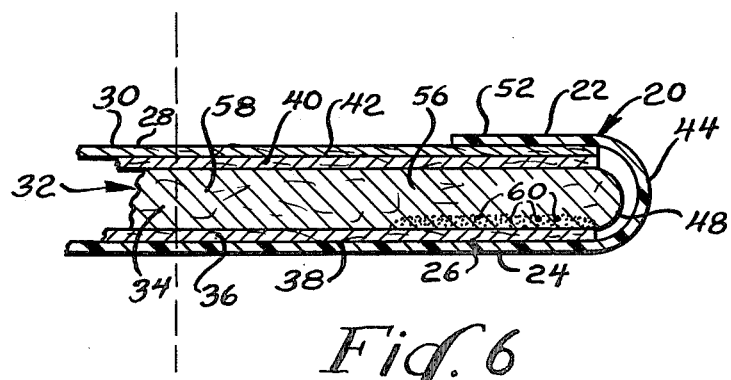
FIG. 6 is a fragmentary sectional view of another embodiment of the article of the present invention.

With reference to FIGS. 1 and 2, the front surface of the pad portion 34 in the side margins 56 may be wetted slightly, and the hydrocolloid material 60 may be placed on the wetted front surface of the pad portion 34 after which the front wadding sheet 40 is positioned over the pad portion 34, such that the hydrocolloid material 60 is located adjacent the front surface 42 of the pad 32 with the moisture facilitating retention of the material 60 in the side margins 56. In an alternative form, with reference to FIG. 6, the hydrocolloid material 60 may be placed against the moistened back surface of the pad portion 34 after which the back wadding sheet 36 is positioned over the back surface of the pad portion 34, such that the hydrocolloid material 60 is positioned adjacent the back surface 38 of the pad 32. In either event, the hydrocolloid material 60 is located in the side or end margins at a position spaced from the fluid receiving region 58 of the pad 32.

In use, the diaper is secured about an infant through use of the tape fasteners 54 in a known manner. During voiding, the urine passes into the pad 32 in the fluid receiving region 58 and spreads to the lateral side margins 56 where the hydrocolloid material absorbs and retains the body fluids at a location spaced from the fluid receiving region 58. Thus, the body fluids are retained at pad locations spaced from the point of application to the diaper, in order to make maximum use of the pad material. Additionally, the fluid receiving region 58 of the pad 32 is substantially free of the hydrocolloid material, in order to prevent formation of a film by the wetted hydrocolloid materials in the region 58 which would otherwise impede passage of body fluids into the pad, thus minimizing the possibility of fluid saturation in the region 58 and accompanying back wetting from the pad through the top sheet against the infant.

Figure 5:
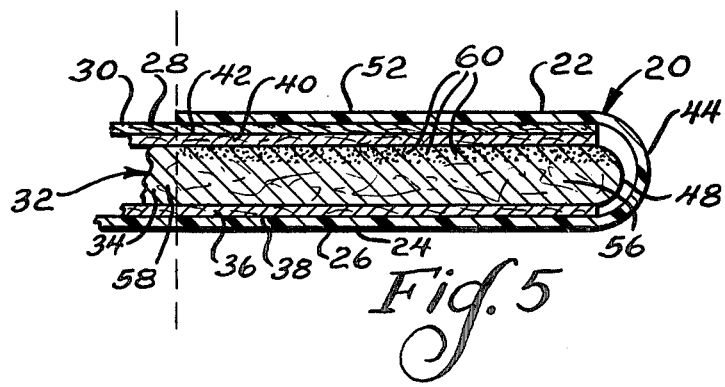
FIG. 5 is a fragmentatry sectional view of another embodiment of the article of the present invention.

Another embodiment of the present inventionn is illustrated in FIG. 5, in which like reference numerals designate like parts. In this embodiment, the lateral margins 52 of the backing sheet 24 extend a sufficient distance inwardly from the side edges 48 of the pad 32 to overlie the lateral pad side margins 56. Thus, the backing sheet side margins 52 cover the pad margins 56 and the hydrocolloid material 60, such that the backing sheet 24 forms fluid impervious pockets which minimize the possibility of leakage from the pad side margins 56 where the fluids are retained by the hydrocolloid material 60.

Figure 4:
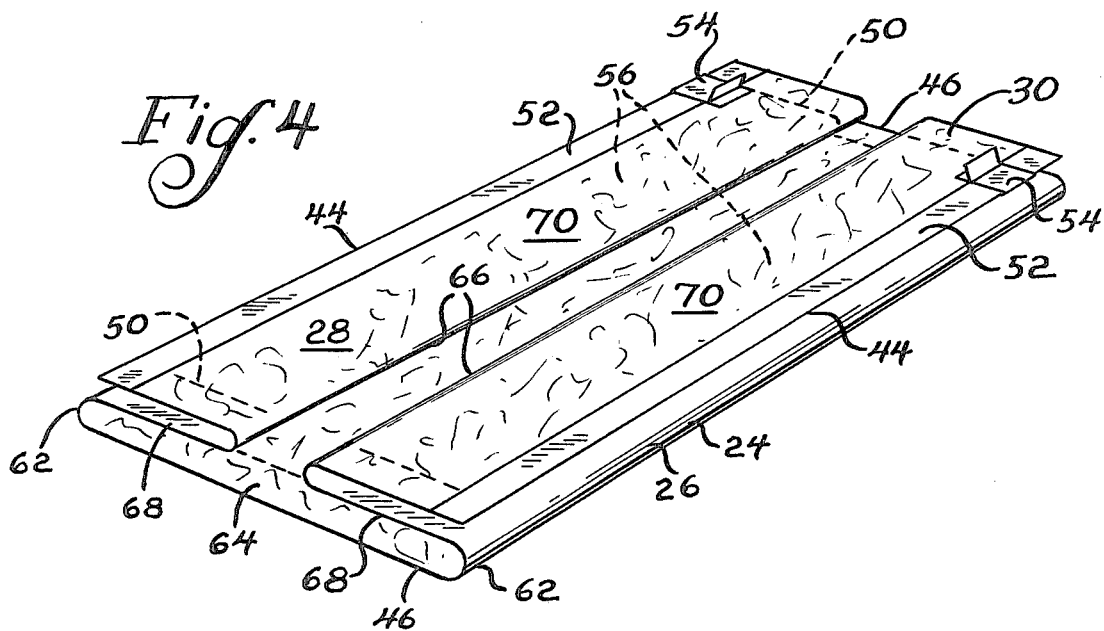
FIG. 4 is a perspective view of the article of FIG. 1 as folded into a box-pleat configuration.

With reference to FIGS. 1, 2, and 4, the diaper may be folded into a box-pleat configuration in a manner described as follows. The pad assembly 22 is folded along a pair of first fold liens 62 defining a longitudinally extending central panel 64 intermediate the fold lines 62, and a pair of second fold lines 66 defining a pair of longitudinal first panels 68 which extend between the fold line 62 and 66 and which overlie the central panel 64. The second fold lines 66 define a pair of outermost panels 70 extending from the second fold lines 66 and overlying the first panels 68. In a preferred form, as shown, the lateral side margins 56 of the pad 32 are located in the outermost panels 70 of the folded diaper, such that the first panels 68 separate the central panel 64 and the hydrocolloid material 60 retained in the outermost panels 70.

The foregoing detailed description is given for clearness of understanding only, and no unnecessary limitations should be understood therefrom, as modifications will be obvious to those skilled in the art.

I claim:

1. A disposable diaper comprising, an absorbent pad assembly having a pair of side edges, a pair of end edges connecting the side edges, a fluid pervious top sheet, a backing sheet of fluid impervious material, and an absorbent pad comprising a mass of fibers located intermediate said top and backing sheets and having a pair of opposed side edges located adjacent the side edges of the pad assembly, said pad assembly having a pair of longitudinal first fold lines defining a longitudinally extending central panel, and a pair of second longitudinal fold lines defining a pair of longitudinally extending first panels located intermediate the first and second fold lines and overlying the central panel, said second fold lines defining a pair of longitudinally extending outermost panels overlying the first panels and located intermediate the second fold lines and the side edges of the pad assembly, with the outermost panels including side margins of the pad, said pad assembly having a hydrocolloid material dispersed in fibers of the pad and positioned in longitudinal central regions of said opposed pad side margins, a pair of opposed pad end margins located adjacent said pair of opposed end edges of the pad assembly, said opposed pad end margins having a hydrocolloid material dispersed in fibers of the pad, with said central panel defining a fluid receiving region and being substantially free of hydrocolloid material, and said diaper having a pair of tape fasteners located adjacent said opposed side edges of the pad assembly and adjacent one of said end edges.

2. The article of claim 1 wherein said hydrocolloid material is located adjacent a front surface of said opposed pad side margins and said opposed pad end margins.

3. The article of claim 1 wherein said hydrocolloid material is located adjacent a back surface of said opposed pad side margins and said opposed pad end margins.

* * * * *